United States Patent [19] … [11] Patent Number: 4,988,817
Madison et al. … [45] Date of Patent: Jan. 29, 1991

[54] PROCESS FOR PREPARATION OF QUATERNARY AMMONIUM AND PHOSPHONIUM SUBSTITUTED CARBONIC ACID ESTERS

[75] Inventors: Stephen A. Madison, Valley Cottage, N.Y.; Jeffrey Bonn, Emerson; Eddie N. Gutierrez, Palisades Park, both of N.J.

[73] Assignee: Lever Brothers Company, Division of Conopco, Inc., New York, N.Y.

[21] Appl. No.: 272,197

[22] Filed: Nov. 16, 1988

[51] Int. Cl.$^5$ .................. C07D 211/42; C07D 211/46; C07C 143/26

[52] U.S. Cl. .................... 546/222; 544/158; 544/383; 544/384; 544/399; 546/301; 546/342; 548/551; 548/556; 548/573; 558/270; 558/271

[58] Field of Search ............... 558/271, 270; 546/222, 546/301, 342; 544/158, 383, 384, 399; 548/551, 556, 573

[56] References Cited

U.S. PATENT DOCUMENTS

| | | | |
|---|---|---|---|
| 3,206,426 | 9/1965 | Keskkula et al. | 558/270 X |
| 3,218,346 | 11/1965 | Baker et al. | 558/270 |
| 3,839,395 | 10/1974 | Otsuka et al. | 558/270 X |
| 4,686,061 | 8/1987 | Nollet et al. | 558/271 X |
| 4,751,015 | 6/1988 | Humphreys et al. | 252/99 |
| 4,818,426 | 4/1989 | Humphreys et al. | 558/271 X |
| 4,931,563 | 6/1990 | Madison et al. | 546/222 |

FOREIGN PATENT DOCUMENTS 1232035  5/1971  United Kingdom ............... 558/271

OTHER PUBLICATIONS

European Search Report and Annex, EP No. 89 20 2735.

Primary Examiner—Mary C. Lee
Assistant Examiner—Fiona T. Powers
Attorney, Agent, or Firm—Milton L. Honig

[57] ABSTRACT

A process is provided for obtaining quaternary ammonium or phosphonium substituted carbonic acid esters. The first step involves reacting the hydroxyl predecessor compound of the ester with phosgene in an aprotic organic solvent to obtain a solution of chloroformate/hydrogen chloride complex. In a second step, the chloroformate/hydrogen chloride complex in solution is admixed with a salt whose conjugate anion, normally a phenol sulfonate, has structure L. During the admixing step, pH is maintained no lower than 6 until all reactants have been combined to form the product ester. Thereupon, pH is lowered to less than 5.5 to stabilize product against hydrolysis.

19 Claims, No Drawings

PROCESS FOR PREPARATION OF QUATERNARY AMMONIUM AND PHOSPHONIUM SUBSTITUTED CARBONIC ACID ESTERS

BACKGROUND OF THE INVENTION

1. Field of the Invention

The invention relates to a process for preparing carbonic acid esters having a quaternary group which esters are useful as bleach precursors in detergent compositions.

2. The Prior Art

Detergent compositions that rely upon sodium perborate as a bleach normally require a precursor to activate the oxygen-releasing compound where wash-water temperatures are below 60° C. A recently issued patent, U.S. Pat. No. 4,751,015 (Humphreys et al.), reported an exceptionally effective bleach precursor family of compounds identified as quaternary ammonium or phosphonium substituted carbonic acid esters. These precursors were reported synthesized in a two-step procedure. For instance, 2-(N,N,N-trimethylammonium)ethyl sodium 4-sulphophenyl carbonate chloride (SPCC) was synthesized by first preparing choline chloroformate chloride through reaction of phosgene with choline chloride in a chloroform solution. The choline chloroformate chloride was then isolated as a crystalline solid. In a second step, the solid choline chloroformate chloride was added to an aqueous solution of sodium 4-phenol sulfonate whose phenolic proton was removed with an equimolar amount sodium hydroxide.

A number of problems are associated with this process. For instance, there are handling problems with choline chloroformate chloride, a highly hygroscopic material. Spontaneous crystallization of the chloroformate from solution has been noted. This presents a challenge in commercial production to avoid pipeline constriction. Furthermore, yields of the final product, SPCC, are variable, sometimes being even quite poor (40-85%). Instability of the final product is a still further problem.

Consequently, it is an object of the present invention to provide an improved process for the synthesis of quaternary ammonium or phosphonium substituted carbonic acid esters.

A more specific object of the present invention is to provide an improved process for obtaining the aforementioned carbonic acid esters which does not necessitate isolation of the intermediate chloroformate chlorides.

A further object of the present invention is to provide a synthesis of carbonic acid esters that results in a high and relatively reproducible product yield.

A still further object of the present invention is to provide a synthesis of carbonic acid esters such that these esters remain stable under reaction conditions.

SUMMARY OF THE INVENTION

A process is provided for preparation of quaternary ammonium and phosphonium substituted carbonic acid esters of the formula:

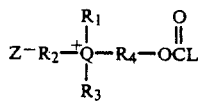

(I)

wherein:

$R_1$, $R_2$ and $R_3$ are each a radical selected from the group consisting of alkyl, alkenyl, alkynyl, cycloalkyl, cycloalkenyl, alkaryl, aryl, phenyl, hydroxyalkyl, polyoxyalkylene, and $R_{hd\ 4}OCOL$;

or two or more of $R_1$, $R_2$, and $R_3$ together form an alkyl substituted or unsubstituted nitrogen-containing heterocyclic ring system;

or at least one of $R_1$, $R_2$, and $R_3$ is attached to $R_4$ to form an alkyl substituted or unsubstituted nitrogen-containing heterocyclic ring system;

$R_4$ is selected from a bridging group consisting of alkylene, cycloalkylene, alkylenephenylene, phenylene, arylene, and polyalkoxylene; and wherein the bridging group can be unsubstituted or substituted with $C_1$-$C_{20}$ atoms selected from alkyl, alkenyl, benzyl, phenyl and aryl radicals;

$Z^-$ is a monovalent or multivalent anion leading to charge neutrality when combined with $Q^+$ in the appropriate ratio and wherein $Z^-$ is sufficiently oxidatively stable not to interfere significantly with bleaching by a peroxy carbonic acid;

Q is nitrogen or phosphorous; and

L is selected from the group consisting of:

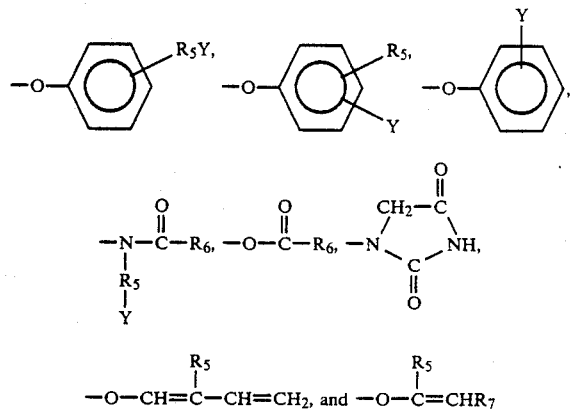

wherein $R_5$ and $R_6$ are a $C_1$-$C_{12}$ alkyl group, $R_7$ is H or $R_5$, and Y is H or a water solubilizing unit selected from the group consisting of $-S^-_3M^+$, $-SO^-_2M^+$, $-N^+(R_5)_3X^-$, $BI_2$, OH, and $O\leftarrow N(R_5)_2$ and mixtures thereof; $M^+$ is a cation which provides solubility to the ester, and $X^-$ is an anion which provides solublity to the ester;

comprising the steps of:

(i) reacting a hydroxyl compound of the formula:

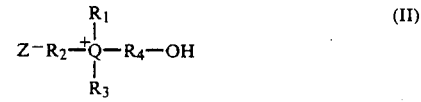

(II)

with phosgene in an aprotic organic solvent to obtain in solution a hydrogen chloride complex of a chloroformate of the formula:

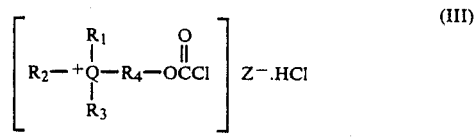

(III)

(ii) admixing said solution of the hydrogen chloride complex of the chloroformate with a salt of a material whose conjugate anion has structure L, maintaining the pH no lower than 6 during said admixing until all reactants have been combined to form ester I, and thereupon lowering pH to less than 5.5 thereby stabilizing said ester in solution.

DETAILED DESCRIPTION OF THE INVENTION

The present invention is an outgrowth of work reported in U.S. Pat. NO. 4,751,015. The first step of the reaction, chloroformate chloride formation, was studied with particular focus upon the choline derivatives. There was one particularly surprising observation with respect to the first step. It was noticed that there was minimal outgassing of hydrogen chloride into alkali traps present to avoid acid emissions. Originally, it was believed that residual hydrogen chloride by-product was being removed in the work-up procedure. Work-up, as noted in Example 1 of U.S. Pat. No. 4,751,015, consisted of water aspirator pressure removal of solvent. Thereafter, the solid product residue was subjected to high vacuum. Removal of hydrogen chloride was thereby believed to have been accomplished However, further study of the reaction indicated excess acidity was present in the subsequent carbonation reaction that employed the resultant solid chloroformate.

Originally, a nuclear magnetic resonance (NMR) spectrum could not be obtained on the solid isolated choline chloroformate chloride because of apparent insolubility in various solvents. With further work, it was now realized that at the end of the reaction, there is a separation into an upper and lower liquid phase. With chloroform as the reaction solvent, the lower liquid phase was nearly all solvent while the upper phase contained some chloroform, hydrogen chloride and choline chloroformate chloride. Essentially no hydrogen chloride was detected in the lower solvent phase. NMR analysis revealed an equimolar ratio of hydrogen chloride to chloroformate strongly indicating complex formation.

The chloroformate/hydrogen chloride complex can be isolated as a solid by one of two procedures. A stream of dry nitrogen can be passed over the liquid reaction phase after separation from the solvent phase. Alternatively, the liquid reaction phase can be seeded with solid chloroformate.

Either technique results in rapid crystallization. The solvent which had been part of this liquid phase is excluded from the resultant solid. Dissolution of the solid chloroformate in acetontrile followed by NMR examination showed essentially no change in the level of hydrogen chloride. The chloroformate/hydrogen chloride precipitate can also be "re-liquified" by suspending in chloroform and bubbling thereinto anhydrous hydrogen chloride.

Upon realization that the chloroformate was in the form of a hydrogen chloride complex, it was also realized that the acid component would have some effect upon the second step of the synthesis. Indeed, much improved, reproducible yields of final ester product were found attainable by co-adding a sacrificial buffer to the carbonation step. This buffer is used to scavenge the hydrogen chloride released from the chloroformate complex. Thus, in addition to one equivalent of sodium hydroxide added to neutralize sodium 4-sulphophenol, as reported in Example 1 of U.S. Pat. No. 4,751,015, a molar equivalent of buffer agent is desirably included in the water reaction medium.

Buffer agent can be added to the second (i.e. carbonation) step either along with the chloroformate/hydrogen chloride complex or at a point subsequent to complex addition The parameter that is important is to keep pH of the carbonation reaction mixture above pH 6, preferably at least 6.5. Below pH of 6, the respective phenolate concentration becomes very low resulting in slow reaction time and decreased yield. With the pH at or above 6, there will be an effective, constant level of phenolate anion present for reaction with chloroformate. Reproducible yields are now easily achieved with use of the buffer.

Typical buffer agents include such alkaline material as sodium carbonate, sodium bicarbonate, sodium mono- and dihydrogen phosphate and the like. The amount of buffer agent relative to the chloroformate chloride/hydrogen chloride complex should be in a molar ratio of about 2:1 to 1:0.9, preferably about 1:1.

A number of solvents may be utilized in the chloroformate first step of the reaction. Of course, the solvent must be an aprotic organic solvent of polar character. Useful solvents include chloroform, methylene chloride, carbon tetrachloride, nitromethane, sulfolane and acetonitrile. Chloroform is the most preferred solvent.

Other factors also influence the reaction. Thus, it has been found preferable not to isolate the chloroformate/hydrogen chloride complex. Rather, it has been found advantageous to add the chloroformate/hydrogen chloride complex in its liquid form still containing certain amounts of solvent. The liquid form of the chloroformate intermediate has benefit in allowing the step two reaction to be homogeneous. Localized regions of low pH cannot occur in a homogeneous medium. This contrasts with the alternative mode where chloroformate chloride is added in solid crystalline form to aqueous phenolate anion. Only where a high degree of agitation is practiced can the solid form be effectively employed.

There is an additional advantage to using chloroformate in solution. As a homogeneous liquid form, the reaction proceeds with great rapidity. Chloroformate can be added nearly as quickly as it can be introduced. Rapid reaction is important to minimize the time within which the carbonic acid ester product must remain under alkaline conditions. For example, at pH 10, the half-life of SPCC at room temperature is 270 seconds. Although the initial pH is near 10.5, the pH decreases as a func. tion of the rate at which chloroformate is introduced since phenolate anion is consumed during the carbonation reaction. This decline in pH during the reaction course will, to a great extent, protect the product from hydrolytic loss.

There is one further process detail which has some impact upon the second step. Where chloroformate is to be used with variable, and perhaps undetermined, levels of hydrogen chloride, either a lesser or greater amount of buffer will be required. A convenient procedure involves addition of the buffer at some point toward the end of the second step. Arbitrarily, we chose pH 8 to begin the addition and then maintain the reaction pH between 6 and 6.5 by judicious introduction of buffer and chloroformate. Alkalinity is controlled until all the chloroformate has been added. In effect, this procedure allows one to control very accurately the amount of buffer without knowing the total acidity of the chloroformate intermediate.

Another quite important aspect of the present process is the final pH adjustment at the end of the final step in the reaction. Thus, at the end of the reaction, the reaction medium pH is dropped to less than 5.5, normally within the pH range of 0 to 5, preferably between 4 and 5.5.

After reducing pH to 4–5.5 and removing solvent, a clear solution normally remains. Isolation of the carbonic acid ester product can be achieved in several ways. These include lyophillization, precipitation with 95% ethanol, and spraydrying. All three methods give a product containing 3 mole equivalents of sodium chloride (36.6 wt. %). Where it becomes necessary to remove the sodium chloride, several washes of the material with warm 95% ethanol was surprisingly found to free product of the salt.

The quaternary ammonium and phosphonium substituted carbonic acid esters produced by the aforementioned process have the general formula:

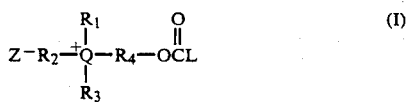

wherein:

$R_1$, $R_2$ and $R_3$ are each a radical selected from the group consisting of alkyl, alkenyl, alkynyl, cycloalkyl, cycloalkenyl, alkaryl, aryl, phenyl, hydroxyalkyl, polyoxyalkylene, and $R_4OCOL$;

or two or more of $R_1$, $R_2$, and $R_3$ together form an alkyl substituted or unsubstituted nitrogen-containing heterocyclic ring system;

or at least one of $R_1$, $R_2$, and $R_3$ is attached to $R_4$ to form an alkyl substituted or unsubstituted nitrogen-containing heterocyclic ring system;

$R_4$ is selected from a bridging group consisting of alkylene, cycloalkylene, alkylenephenylene, phenylene, arylene, and polyalkoxylene; and wherein the bridging group can be unsubstituted or substituted with $C_1-C_{20}$ atoms selected from alkyl, alkenyl, benzyl, phenyl and aryl radicals;

$Z^-$ is a monovalent or multivalent anion leading to charge neutrality when combined with $Q^+$ in the appropriate ratio and wherein $Z^-$ is sufficiently oxidatively stable not to interfere significantly with bleaching by a peroxy carbonic acid;

Q is nitrogen or phosphorous; and

L is selected from the group consisting of:

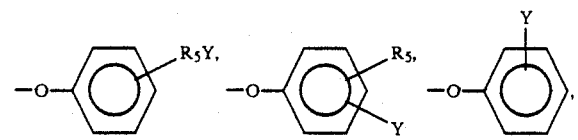

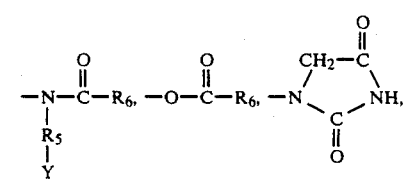

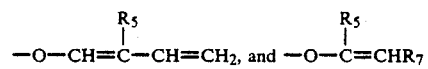

wherein $R_5$ and $R_6$ are a $C_1-C_{12}$ alkyl group, $R_7$ is H or $R_5$, and Y is H or a water solubilizing unit selected from the group consisting of $-SO^-_3M^+$, $-COO^-M^+$, $-SO^-_2M^+$, $-N^+(R_5)_3X^-$, $NO_2$, OH, and $O \leftarrow N(R_5)_2$ and mixtures thereof; $M^+$ is a cation which provides solubility to the ester, and $X^-$ is an anion which provides solubility to the ester.

Most preferred of the leaving groups (L) is the phenol sulfonate type. Especially preferred is the 4-sulphophenol group. Sodium, potassium and ammonium cations are the preferred counterions to the sulphophenol structures.

Although phosphonium groups where Q is phosphorous is within the scope of this invention, for economic reasons it is most preferred that Q be nitrogen. Furthermore, the precursor and respective peracid derivative compounds should preferably contain a quaternary ammonium carbon surrounded by $R_1$, $R_2$ and $R_3$ each the same or different and having $C_1-C_{20}$ atom radicals selected from the group consisting of alkyl, alkylaryl, benzyl, hydroxyalkyl, heterocyclic rings containing the quaternary nitrogen groups where $R_1$ and $R_4$ or $R_1$ and $R_2$ are joined together, and mixtures of groups thereof.

In particular, it is desirable that $R_1$ be a short-chain $C_1-C_4$ alkyl radical, preferably methyl, while $R_2$ and $R_3$ be a longer chain $C_7-C_{20}$ alkyl or alkylaryl, such as stearyl, lauryl, or benzyl group. With regard to the $R_4$ bridge between the quaternary nitrogen and carbonate groups, it is desirable that $R_4$ be a bridging group selected from $C_2-C_{20}$ alkylene, $C_6-C_{12}$ henylene, $C_5-C_{20}$ cycloalkylene, and $C_8-C_{20}$ alkylenephenylene groups. Preferably, the alkylene groups should have carbon atoms. Further, the bridging group can be unsubstituted or substituted with $C_1-C_{20}$ alkyl, alkenyl, benzyl, phenyl and aryl radicals.

Within the context of this invention, there may be compounds having the general structure (I) where $R_1$ and $R_4$ together or $R_1$ and $R_2$ together form an alkyl substituted or unsubstituted nitrogen-containing heterocyclic ring system. Representative of these systems are rings defining pyridine, morpholine, pyrrolidine, piperidine and piperazine.

More specific compounds are listed in U.S. Pat. No. 4,751,015 which is herein incorporated by reference.

The process is described generally as comprising the steps of:

(i) reacting a hydroxyl compound of the formula:

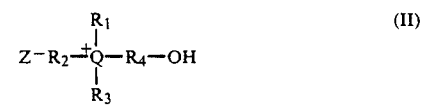

with phosgene in an aprotic organic solvent to obtain in solution a hydrogen chloride complex of a chloroformate of the formula:

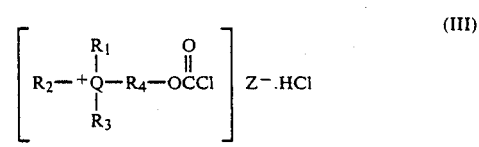

(ii) admixing said solution of the hydrogen chloride complex of the chloroformate with a salt of a material whose conjugate anion has structure L, maintaining the pH no lower than 6 during said admixing until all reactants have been combined to form ester I and thereupon lowering pH to less than 5.5 thereby stabilizing said ester in solution.

Structure L, conjugate anion, is as previously described. Conjugate cations of salts of L include the alkali metal, alkaline earth metal, ammonium and alkylammonium cations. Preferred cations are those of sodium, ammonium, triethanolammonium and triethylammonium ions.

The following examples will more fully illustrate the embodiments of this invention. All parts, percentages and proportions referred to herein and in the appended claims are by weight unless otherwise illustrated.

EXAMPLE 1

Preparation of Choline Chloroformate Chloride/Hydrogen Chloride Complex $$[(CH_3)_3\overset{+}{N}CH_2CH_2OCOCl]Cl^-.HCl$$

A 500 ml three-neck flask was equipped with a mechanical stirrer, a dry ice/acetone condenser fitted with an outlet adaptor leading to two series connected sodium hydroxide solutions scrubber bottles, and an inlet adaptor connected to a flask containing liquefied phosgene. The phosgene which had been distilled was employed in the amount of 30.3 ml (42 grams, 0.43 mole, 20 mole % excess) and supplied by AGL Welding Company. Into the flask was placed 150 ml of ethanol-free, chilled chloroform. Ethanol had been removed from the chloroform by washing several times with an equal volume of distilled-deionized water. The chloroform was then dried over anhydrous calcium chloride. Chloroform used without purification will lead to the formation of ethyl cholyl carbonate.

To the phosgene solution was introduced 50 grams (0.357 mole) of dry choline chloride (ex Aldrich). Choline chloride was dried by heating in a vacuum oven at 60° C. for several days. At the end of this drying period, NMR analysis revealed the choline chloride to have approximately 5 mole % water. No heat was evolved during the rapid addition of the choline salt. After about 30 minutes, the choline chloride took on a tacky appearance. After about one hour, the formation of two clear liquid phases occurred. During the phase change, enough heat evolved to reflux the phosgene. The exotherm was quickly brought under control with an ice bath. After quenching the exotherm, the reaction was allowed to continue for an additional one hour. The reaction was essentially complete at this time; confirmation of which was made by NMR analysis of the upper product phase. Upper from lower solvent phases were separated. Product was in the upper phase and stored under nitrogen in a tightly capped sample jar. Product which was kept at ambient temperature appeared to be stable over the course of several weeks. Proton NMR of the upper phase exhibited peaks 3.55 ppm (S, (CH$_3$)$_3$), 4.2 ppm (m, $\overset{+}{N}$CH$_2$), 5.05 ppm (m, CH$_2$O) and 12.8 ppm (S, HCl) (internal standard methylene chloride. C-13 NMR of the same material displayed peaks at 56.2 pm (CH$_3$)$_3$, 66.1 ppm (CH$_2$O), 67.7 ppm ($\overset{+}{N}$CH$_2$), and 152.2 ppm (OCOCl) (internal standard sulfolane).

EXAMPLE 2

Preparation of 2-(N,N N-TrimethYlammonium)EthYl Sodium 4-Sulfophenyl Carbonate Chloride (SPCC)

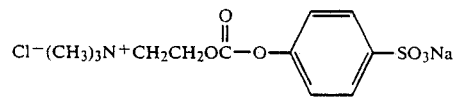

A 150 ml beaker was charged with 25 ml distilled-deionized water, 1.08 gms (27 mmoles) of sodium hydroxide and 6.27 gms (27 mmoles) of sodium 4-sulfophenol dihydrate (ex Eastman). The pH of this solution was near 10.7. When complete solubilization had occurred, the solution was chilled to 5° C. A separate base solution was prepared by adding 7.1 gms (67 mmoles) sodium carbonate to 100 ml distilled-deionized water, placed in a dropping tunnel and situated over the beaker containing the sulfophenolate solution. An amount (determined by NMR analysis) of cholyl chloroformate chloride/hydrogen chloride/chloroform (or methylene chloride) solution corresponding to 27 mmoles of chloroformate was introduced to the sulfophenolate solution by peristaltic action (Cole-Palmer Masterflex Model 7020-50). A positive pressure of dry nitrogen was maintained over the reservoir of cholyl chloroformate. The chloroformate was added rapidly at the start until pH fell to near 8. Then the addition rate was slowed since pH changed rapidly at this point and became more difficult to control. Undoubtedly, the difficulty was due to a lack of bu(fering which was not the case at the higher pH 25 since the sulfophenolate/sulfophenol acted as a buffer. As the pH reached 6.5-7, the addition of carbonate solution was begun and pH maintained at this level until all the chloroformate had been added. After chloroformate addition was complete, the pH was adjusted to 4-5.5 with 1N hydrochloric acid. In this state the solution was quite stable. The halosolvent phase was separated and the aqueous product phase worked up by either lyophillization or adding four volume equivalents of 95% ethanol to precipitate the SPCC product. NMR analysis indicated nearly quantitative conversion.

EXAMPLE 3

A series of experiments were performed to evaluate the influence of pH on the carbonation step wherein sodium 4-sulphophenol is reacted with cholyl chloroformate chloride/hydrogen chloride complex. Details of the reaction were essentially identical to that outlined in Example 2 except for modifying the amounts of sodium carbonate added to control pH. Table I delineates the relationship of pH and the percent yield of 2-(N,N,N-trimethylammonium)ethyl sodium 4-sulphophenyl carbonate chloride.

TABLE I

| Dependence of SPCC Yield on pH | |
|---|---|
| pH | % Yield |
| 5.5–6.0 | 89 |
| 5.0–5.5 | 87.5 |
| 4.0–5.0 | 76 |
| 2.5–4.0 | 68 |

From Table I, it is evident that at pH less than 5.5 there is a very substantial reduction in product yield.

EXAMPLE 4

Investigation of the carbonation step revealed a further process limitation. It was found that under the procedure as illustrated in Example 2 upon completion of the cholyl chloroformate addition, product yield would vary depending upon the final pH under which the mixture was maintained. Table II outlines the dependence of yield on the final solution pH under which the product was temporarily stored prior to work-up.

TABLE II

Product Stability Versus pH

| Final pH | Yield (%)* |
| --- | --- |
| 4 | 88 |
| 7 | 58 |

*Yield after 17 hours in solution at room temperature; normal yield at end of reaction (0 hours) was 92%.

The foregoing description and examples illustrate selected embodiments of the present invention. In light thereof, various modifications will be suggested to one skilled in the art, all of which are within the spirit and purview of this invention.

What is claimed is:

1. A process for preparation of quaternary ammonium and phosphonium substituted carbonic acid esters of the formula:

wherein:

$R_1$, $R_2$ and $R_3$ are each a radical selected from the group consisting of alkyl, alkenyl, alkynyl, cycloalkyl, cycloalkenyl, alkaryl, aryl, phenyl, hydroxyalkyl, polyoxyalkylene, and $R_4OCOL$;

or two or more of $R_1$, $R_2$, and $R_3$ together form an alkyl substituted or unsubstituted nitrogen-containing heterocyclic ring system;

or at least one of $R_1$, $R_2$, and $R_3$ is attached to $R_4$ to form an alkyl substituted or unsubstituted nitrogen-containing heterocyclic ring system;

$R_4$ is selected from a bridging group consisting of alkylene, cycloalkylene, alkylenephenylene, phenylene, arylene, and polyalkoxylene; and wherein the bridging group can be unsubstituted or substituted with $C_1$–$C_{20}$ atoms selected from alkyl, alkenyl, benzyl, phenyl and aryl radicals;

$Z^-$ is a monovalent or multivalent anion leading to charge neutrality when combined with $Q^+$ in the appropriate ratio and wherein $Z^-$ is sufficiently oxidatively stable not to interfere significantly with bleaching by a peroxy carbonic acid;

Q is nitrogen or phosphorous; and

L is selected from the group consisting of:

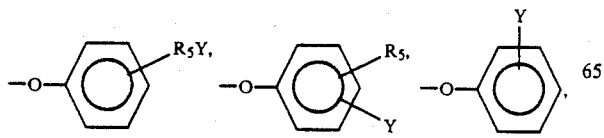

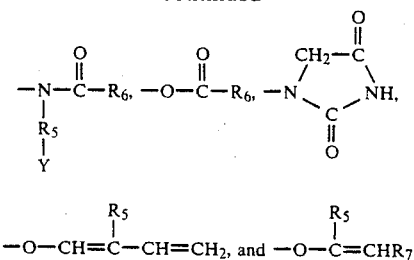

wherein $R_5$ and $R_6$ are a $C_1$–$C_{12}$ alkyl group, $R_7$ is H or $R_5$, and Y is H or a water solubilizing unit selected from the group consisting of —$SO_3^-M^+$, —$COO^-M^+$, —$SO_2^-M^+$, —$N^+(R_5)_3X^-$, $NO_2$, OH, and O←$N(R_5)_2$ and mixtures thereof; $M^+$ is a cation which provides solubility to the ester, and $X^-$ is an anion which provides solubility to the ester;

comprising the steps of:

(i) reacting a hydroxyl compound of the formula:

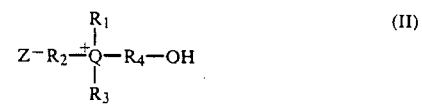

with phosgene in an aprotic organic solvent to obtain in solution a hydrogen chloride complex of a chloroformate of the formula:

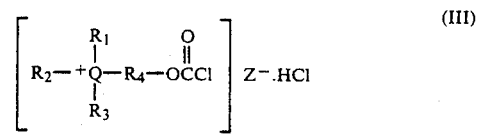

(ii) admixing said solution of the hydrogen chloride complex of the chloroformate with a salt of a material having structure L≠H maintaining the pH no lower than 6 during said admixing until all reactants have been combined to form ester I, and thereupon lowering pH to less than 5.5 thereby stabilizing said ester in solution.

2. A process according to claim 1 wherein said solvent is selected from the group consisting of chloroform, methylene chloride, carbon tetrachloride, perchloroethylene, nitromethane, sulfolane and acetonitrile.

3. A process according to claim 1 wherein pH is maintained no lower than 6.5 with the aid of a buffer agent selected from sodium carbonate, sodium bicarbonate, sodium mono- and dihydrogen phosphate.

4. A process according to claim 1 wherein $M^+$ is a hydrogen, alkali metal, ammonium or alkyl or hydroxyalkyl substituted ammonium cation, and $X^-$ is a halide, hydroxide, phosphate, sulfate, methyl sulfate or acetate anion.

5. A process according to claim 1 wherein L has the formula:

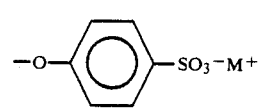

wherein $M^+$ is a sodium, potassium or ammonium cation.

6. A process according to claim 1 wherein Q is nitrogen and $R_1$, $R_2$ and $R_3$ are each the same or different and selected from $C_1$-$C_{20}$ atom radicals selected from the group consisting of alkyl, alkylaryl, benzyl, hydroxyalkyl, and heterocyclic rings containing the quaternary nitrogen where $R_1$ and $R_4$ or $R_1$ and $R_2$ are joined together, and mixtures of groups thereof.

7. A process according to claim 6 wherein $R_1$ is selected from short-chain $C_1$-$C_4$ alkyl radicals.

8. A process according to claim 7 wherein $R_2$ and $R_3$ are each a longer chain $C_7$-$C_{20}$ alkyl or alkylaryl radical.

9. A process according to claim 8 wherein said longer chain radical is selected from the group consisting of benzyl, lauryl and stearyl groups.

10. A process according to claim 1 wherein $R_4$ is selected from a bridging group consisting of $C_2$-$C_{20}$ alkylene, $C_6$-$C_{12}$ phenylene, $C_6$-$C_{20}$ cycloalkylene, and $C_8$-$C_{20}$ alkylphenylene groups.

11. A process according to claim 10 wherein the $R_4$ bridging group is a $C_2$-$C_6$ alkylene or $C_6$-$C_{12}$ phenylene group.

12. A process according to claim 6 wherein said heterocyclic ring is selected from pyridine, morpholine, pyrrolidone, piperidine and piperazine.

13. A process according to claim 1 wherein Y is a sulfonic acid salt.

14. A process according to claim 1 wherein the ester product is 2-(N,N,N-trimethylammonium)ethyl sodium 4-sulfophenyl carbonate salt.

15. A process according to claim 1 wherein the ester product is 2-(N-benzyl-N,N-dimethylammonium)ethyl sodium 4-sulfophenyl carbonate salt.

16. A process according to claim 1 wherein the ester product is 2-(N-butyl-N,N-dimethylammonium)ethyl sodium 4-sulfophenyl carbonate salt.

17. A process according to claim 1 wherein the ester product is 2-[4-(N,N,N-trimethylammonium)phenyl]ethyl sodium 4-sulfophenyl carbonate salt.

18. A process according to claim 1 wherein the ester product is sodium 3-(1,1-dimethylpiperidinium) 4-sulfophenyl carbonate salt.

19. A process according to claim 1 wherein the ester product is sodium 4-(1,1-dimethylpiperidinium) 4-sulfophenyl carbonate salt.

* * * * *